United States Patent [19]

Welter et al.

[11] 4,418,069
[45] Nov. 29, 1983

[54] BENZISOSELENAZOLONES AND PROCESS FOR THE TREATMENT OF RHEUMATIC AND ARTHRITIC DISEASES USING THEM

[75] Inventors: André Welter, Cologne, Fed. Rep. of Germany; Léon Christiaens, Nandrin, Belgium; Ferdinand Wirtz-Peitz, Cologne, Fed. Rep. of Germany

[73] Assignee: A. Nattermann & Cie GmbH, Cologne, Fed. Rep. of Germany

[21] Appl. No.: 281,719

[22] Filed: Jul. 9, 1981

[30] Foreign Application Priority Data

Jul. 17, 1980 [DE] Fed. Rep. of Germany ....... 3027075

[51] Int. Cl.³ .................... A61K 31/41; C07D 293/10; C07D 293/12
[52] U.S. Cl. .................................. 424/269; 548/120; 548/121; 549/441; 564/166; 564/177; 564/184; 564/185; 564/186
[58] Field of Search ....................... 548/100, 120, 121; 424/269, 335

[56] References Cited

FOREIGN PATENT DOCUMENTS

| | | | |
|---|---|---|---|
| 670 | 2/1979 | European Pat. Off. ............ | 424/335 |
| 3027074 | 2/1982 | Fed. Rep. of Germany . | |
| 3027075 | 2/1982 | Fed. Rep. of Germany . | |
| 1213401 | 11/1970 | United Kingdom ................ | 424/335 |

OTHER PUBLICATIONS

Lesser, et al., Chemische Berichte, 57B, pp. 1077–1082 (1924).

Weber, et al., Bull. Soc. Chim. France, 1976, (7–8, Pt. 2), pp. 1124–1126 (1976).
Krauss, et al., Das Deutsche Gesundheitswesen, (1979), vol. 34, (37), pp. 1713–1718 and 1769–1773.

Primary Examiner—Diana G. Rivers
Attorney, Agent, or Firm—Pearne, Gordon, Sessions, McCoy, Granger & Tilberry

[57] ABSTRACT

The present invention is related to new benzisoselenazolones having the general formula I

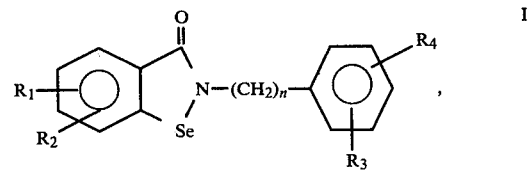

new products having the general formula II

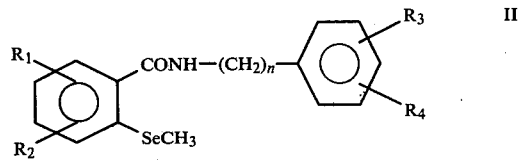

used as intermediary products in the production of the compounds of formula I and a method for the treatment of rheumatic diseases using a compound of formula I as active agent.

4 Claims, No Drawings

BENZISOSELENAZOLONES AND PROCESS FOR THE TREATMENT OF RHEUMATIC AND ARTHRITIC DISEASES USING THEM

The present invention is related to new benzisoselenazolones, process for producing the same, new intermediary products in their production as well as to the use of such new benzisoselenazolones as active agents in pharmaceutical preparations, in particular in anti-inflammatory and anti-rheumatic drugs.

The benzisoselenazolones according to the present invention correspond to the general formula I

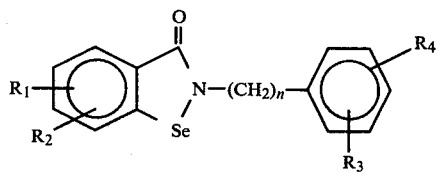

wherein $R_1$ and $R_2$ which may be the same or different from each other, represent hydrogen, fluorine, chlorine, bromine, $C_1$ to 4-alkyl such as methyl or ethyl; $C_1$ to 4-alkoxy such as methoxy; hydroxy, trifluoromethyl or nitro or, two neighbouring substituents together, i.e. $R_1$ and $R_2$ together represent the methylenedioxy group —O—$CH_2$—O—, $R_3$ and $R_4$ which may be the same or different from each other, represent hydrogen, fluorine, chlorine, bromine, $C_1$ to 4-alkyl, $C_1$ to 4-alkoxy, hydroxy, trifluoromethyl, nitro, di-($C_1$ to 4-alkyl)-amino or $R_3$ and $R_4$ together represent the methylenedioxy group —O—$CH_2$—O— or $R_3$ is hydrogen with $R_4$ being —CN, —$COOR_5$ or

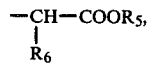

$R_5$ being hydrogen, an alkali metal ion such as a potassium or in particular a sodium ion, or $C_1$ to 4-alkyl and $R_6$ being hydrogen, methyl or ethyl, and n represents 0 or an integer from 1 to 4; from this definition there are excluded and disclaimed the known compounds 2-phenyl-, 2-o-tolyl- and 2-benzyl-1.2-benzisoselenazol-3(2H)-one, i.e. those compounds of the above general formula I wherein n is 0, $R_1$, $R_2$ and $R_3$ are hydrogen, and $R_4$ is hydrogen or o-methyl, or n is 1 and $R_1$, $R_2$, $R_3$ and $R_4$ are hydrogen.

The preferred compounds among the benzisoselenazolones of the general formula I are those wherein n is 0 and either $R_1$ and $R_2$ or $R_1$ and $R_3$ represent hydrogen while the other substituents ($R_3$ and $R_4$ or, respectively, $R_2$ and $R_4$) represent fluorine, chlorine, bromine, hydroxy, methoxy, methyl, trifluoromethyl and/or nitro.

Another preferred group of benzisoselenazolones of the general formula I are those wherein n is 0 or an integer from 1 to 4, $R_1$, $R_2$ and $R_3$ represent hydrogen and $R_4$ is —CN, —$COOR_5$ or

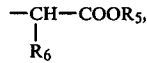

$R_5$ being H, $Na^\oplus$, —$CH_3$ or —$C_2H_5$ and $R_6$ being H, —$CH_3$ or —$C_2H_5$.

Preferred substituents of the nitrogen atom of the isoselenazolone ring in the compounds according to the present invention are for instance:

with n being 0: 4-fluorophenyl, 4-chlorophenyl, 4-hydroxyphenyl, 4-methoxyphenyl, 4-methylphenyl, 4-trifluoromethylphenyl, 4-nitrophenyl, 4-dimethylaminophenyl, 3-bromo-4-hydroxy-phenyl, 3.4-methylenedioxyphenyl, 2-hydroxyphenyl, 3-hydroxyphenyl, 2-fluorophenyl and 3-methoxyphenyl;

with n different from 0: 2-(4-fluorophenyl)-ethyl, 4-phenylbutyl, 3-phenylpropyl, 2-phenylethyl and 4-(4-chlorophenyl)-butyl;

with n being 0 and $R_3$ being hydrogen: 4-hydroxycarbonylphenyl, 4-ethoxycarbonylphenyl, 4-hydroxycarbonylmethylphenyl, 4-ethoxycarbonylmethylphenyl, 4-[1-(hydroxycarbonyl)-ethyl]-phenyl, 4-[1-(ethoxycarbonyl)-ethyl]-phenyl and 4-cyanophenyl.

The present invention is further related to new intermediary products for the production of the benzisoselenazolones of formula I. Such intermediary products correspond to the general formula II

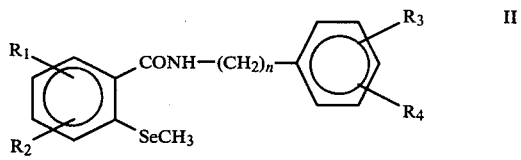

wherein $R_1$ to $R_4$ and n have the same meaning as in formula I.

The benzisoselenazolones of formula I of the present invention may be used in the treatment of numerous diseases. For instance they are useful in the prophylactic treatment or cure of infectious diseases, for the therapeutical treatment of malign tumors, for the stimulation of the immunological system or in the treatment of selenium deficiency diseases as they are defined in W. KRAUSS and P. OEHME, Das Deutsche Gesundheitswesen 1979, vol. 34 (37), pgs. 1713 to 1718 and 1979, vol. 34 (37), pgs. 1769 to 1773.

The benzisoselenazolones of formula I are however in particular characterized by their anti-arteriosclerotic and anti-inflammatory properties. They are therefor in particular useful in the therapy of rheumatic diseases such as arthroses or chronical polyarthritis. The new compounds are characterized by a very good compatibility since they have a low toxicity and, contrary to known anti-inflammatory agents, do not cause formation of ulcera or gastrointestinal irritations.

The new compounds according to the present invention having the formula I surprisingly together with a very good anti-inflammatory activity show a substantially increased therapeutic range over the compounds known up to now in this field of application. Furthermore, they show no undesired side effects such as heartburn, formation of ulcera, intestinal bleedings and the like. They furthermore have a very low toxicity $LD_o$ 2500 to 5000 mg./kg. (p.o. in mice or rats). This is all the more surprising since selenium compounds generally are considered as very toxic compounds.

The new benzisoselenazolones of the present invention having the general formula I may be produced as follows:

(a) a 2-methylseleno-benzoic acid having the general formula III

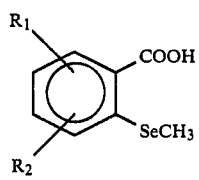

wherein $R_1$ and $R_2$ have the same meaning as in formula I, is subjected to reaction with an inorganic acid chloride, the resulting benzoyl chloride having the general formula IV

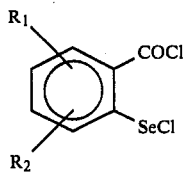

wherein $R_1$ and $R_2$ have the same meaning as in formula I, is subjected to reaction with an amine having the general formula V

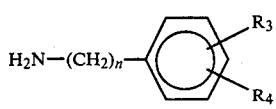

wherein $R_3$, $R_4$ and n have the same meaning as in formula I, under ring closure conditions to yield the benzisoselenazolones of the general formula I, or (b) a 2-methylseleno-benzamide having the general formula II is subjected to ring closure in the presence of an inorganic acid chloride to yield a 3-chloro-1.2-benzisoselenazolonium compound having the general formula VI

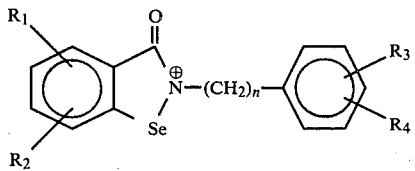

wherein $R_1$, $R_2$, $R_3$, $R_4$ and n have the same meaning as in formula I and thereafter the compound of formula VI is subjected to hydrolysis to yield the corresponding benzisoselenazolone of formula I or (c) a 2-methylseleno-benzamide having the general formula II is subjected to reaction with bromine and thereafter is heated, possibly in the presence of an organic acid or base, and the resulting benzisoselenazolone of formula I finally is separated from the reaction mixture.

The embodiment (a) of the present process corresponds in its process conditions to R. LESSER and R. WEISS, Ber. 57 (1924), pgs. 1077 to 1082 and R. WEBER and M. RENSON, Bull.Soc.Chim.France 1976 (7/8) pgs. 1124 to 1126. Starting compounds according to formula III may be for instance:

2-Methylseleno benzoic acid
2-Methylseleno-4-methyl benzoic acid
2-Methylseleno-4-fluoro benzoic acid
2-Methylseleno-4-chloro benzoic acid
2-Methylseleno-4-methoxy benzoic acid
2-Methylseleno-5-nitro benzoic acid
2-Methylseleno-5-chloro benzoic acid
2-Methylseleno-3-methoxy benzoic acid
2-Methylseleno-4-trifluoromethyl benzoic acid
2-Methylseleno-5-methoxy benzoic acid
2-Methylseleno-6-methoxy benzoic acid
2-Methylseleno-4.5-dichloro benzoic acid
2-Methylseleno-3.4-methylenedioxy benzoic acid
2-Methylseleno-3.4-dimethyl benzoic acid
2-Methylseleno-3.4-dichloro benzoic acid The embodiment (b) of the present process and its detailed process conditions correspond to R. WEBER and M. RENSON, Bull. Soc. Chim. France 1976 (7/8), pgs. 1124 L to 1126.

The new intermediary products according to the present invention having the formula II may be obtained by subjecting a 2-methylseleno benzoic acid of general formula III to reaction with a dichloromethylalkylether, in particular a dichloromethyl lower alkyl ether and, in particular and therefor preferred, to reaction with dichloromethylmethylether and subjecting the resulting 2-methylseleno benzoic acid chloride of the general formula VII

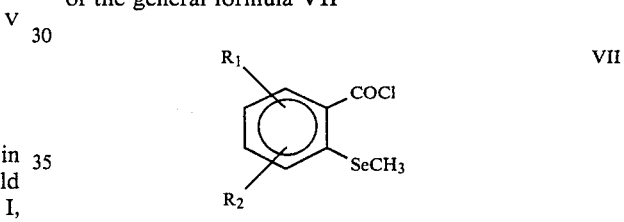

wherein $R_1$ and $R_2$ have the same meaning as in formula I, to reaction with an amine of the general formula V, possibly in the presence of an acid binding agent.

The benzisoselenazolones according to the present invention having the general formula I may be furthermore produced by the embodiment (c) of the present process using as inorganic acid chloride for instance and in particular phosphorus pentachloride.

The benzisoselenazolones according to the present invention having the general formula I may be converted in usual manners to pharmaceutical preparations. For instance, the active agent of formula I may be used as such or in combination with suitable usual pharmaceutical diluents and/or carrier materials which are admixed as usual. The compounds according to the present application may be used in human and veterinary medicine in any usual form, for instance systemically, provided that the formation and upkeep of a sufficient blood or tissue level of the active agent is secured. This may be achieved with oral or rectal or parenteral administration at suitable dosages. Preferably, the applied pharmaceutical preparation is for single dosage administration in accordance with the desired manner of administration, for instance as tablet, dragee, capsule, suppository, granulate, solution, emulsion, suspension, sol or gel. The compounds according to the present application in general are administered in dosages ranging from 10 to 1000 mg. per day, preferably from 30 to 300 mg. per day. The daily dose may be administered in a single dose or split into several dosages. The daily dose preferably is subdivided into two or three dosages per day.

Suitable carrier materials which may be used in the preparation of pharmaceutical products to be orally administered, for instance as tablets, capsules, granulates or powders, are for instance calcium carbonate, calcium phosphate, starch, sugar, lactose, talcum, magnesium stearate, gelatine, polyvinylpyrrolidone, gum arabic, sorbitol, microcristalline, cellulose, polyethyleneglycol, carboxymethyl cellulose, shellac and the like. The tablets may be coated in usual manners. Liquid products for oral application may be aqueous or oily suspensions or solutions, sirups, elixirs or the like. Such products are produced in usual manners. For administration by injection there may be used aqueous or oily suspensions or solutions, powderous products admixed with a filler or lyophilised products which are dissolved before administration. Such products are produced in usual manner.

The new products according to the present invention having the general formula I may also be applied rectally as suppositories which further contain pharmaceutically acceptable carrier materials as they are known for this purpose, for instance polyethylene glycol, lanoline, coconut butter, Witepsol ® or the like. External pharmaceutical preparations are preferably produced as ointments or cremes in usual manners using usual components.

The following Examples serve to further illustrate the present invention without however limiting the same thereto.

EXAMPLE 1

2-(4-Methylphenyl)-1.2-benzisoselenazol-3(2H)-one

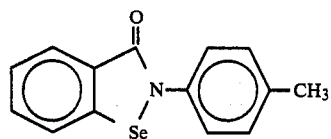

5.54 g. of p-toluidine dissolved in 100 cc. of carbontetrachloride are added dropwise with stirring and ice-cooling (temperature below 10° C.) under a nitrogen atmosphere to a solution of 4 g. of o-chloroselenobenzoic acid chloride dissolved in 80 cc. of carbontetrachloride. After termination of the addition stirring is continued for one hour. The resulting precipitate is filtered off, consecutively washed with a small amount of carbontetrachloride, 0.5 N-hydrochloric acid and water, thereafter is dried and then is recrystallized from carbontetrachloride.

Yield: 4.0 g. (90% of the theoretical). F.p.: 173° to 174° C.

o-Chloroselenobenzoic acid chloride was obtained by reacting o-methylselenobenzoic acid with thionylchloride as described in A. RUWET and M. RENSON, Bull. Soc. Chim. Belg. 1966, vol. 75, pgs. 157 to 168.

As described in Example 1, the following compounds were produced, using the correspondingly substituted aniline derivative:

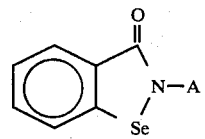

| Example No. | —A | Emperical formula | Yield % of the theoretical | F.p., °C. |
| --- | --- | --- | --- | --- |
| 2 | —⌬—F | $C_{13}H_8FNOSe$ | 69 | 179 to 180 |
| 3 | —⌬—Cl | $C_{13}H_8ClNOSe$ | 72 | 185 to 186 |
| 4 | —⌬—OCH$_3$ | $C_{14}H_{11}NO_2Se$ | 65 | 181 to 184 |
| 5 | —⌬—NO$_2$ | $C_{13}H_8N_2O_3Se$ | 66 | 286 |
| 6 | —⌬—COOC$_2$H$_5$ | $C_{16}H_{13}NO_3Se$ | 71 | 199 to 201 |
| 7 | —⌬—CH(CH$_3$)—COOC$_2$H$_5$ | $C_{18}H_{17}NO_3Se$ | 60 | 176 |
| 8 | —⌬(F) | $C_{13}H_8FNOSe$ | 75 | 165 to 167 |

-continued

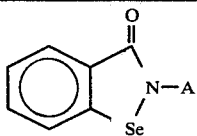

| Example No. | —A | Emperical formula | Yield % of the theoretical | F.p., °C. |
|---|---|---|---|---|
| 9 | —C₆H₄—CH₂—COOC₂H₅ | $C_{17}H_{15}NO_3Se$ | 72 | 167 to 169 |
| 10 | (methylenedioxyphenyl) | $C_{14}H_9NO_3Se$ | 63 | 204 to 206 |
| 11 | (2-methoxyphenyl) OCH₃ | $C_{14}H_{11}NO_2Se$ | 63 | 162 to 164 |
| 12 | (cyclohexyl)—CN | $C_{14}H_8N_2OSe$ | 58 | 230 to 232 |

EXAMPLE 13
2-(4-Dimethylaminophenyl)-1.2-benzisoselenazolon-3-(2H)-one

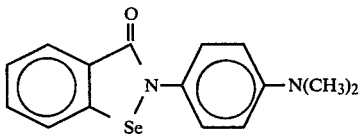

A solution of 2.8 g. of 4-dimethylaminoaniline and 3.2 g. of triethylamine in 60 cc. of carbontetrachloride are added dropwise with stirring and ice cooling (temperature below 10° C.) under a nitrogen atmosphere to a solution of 3.82 g. of o-chloroselenobenzoic acid chloride in 30 cc. of carbontetrachloride. After termination of the addition, stirring is continued for another hour at room temperature. The resulting precipitate is filtered off, dried and stirred with a small amount of water. The insoluble crude final product is recrystallized from toluene/hexane.

Yield: 2.8 g. (59% of the theoretical). F.p.: 220° to 222° C.

EXAMPLE 14
2-(4-Hydroxyphenyl)-1.2-benzisoselenazol-3(2H)-one

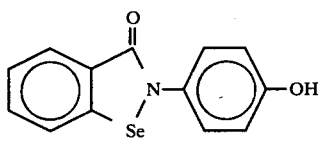

4.58 g. of 4-aminophenol dissolved in 200 cc. of tetrahydrofurane (THF) and 2 cc. of pyridine are added with stirring and ice-cooling (temperature below 10° C.) under a nitrogen atmosphere to a solution of 3.3 g. of o-chloroselenobenzoic acid chloride in 30 cc. of THF. After termination of the addition, the mixture is stirred at room temperatur, the solvent is evaporated under vacuum and the residue is pured into a mixture of ice and dilute hydrochloric acid. The resulting precipitate is filtered off and is recrystallized from ethanol.

Yield: 2.3 g. (61% of the theoretical). F.p.: 253° to 254° C.

EXAMPLE 15
2-(3-Hydroxyphenyl)-1.2-benzisoselenazol-3(2H)-one

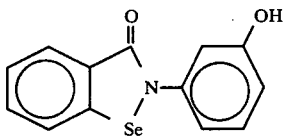

As described in Example 14, 2-(3-hydroxyphenyl)-1.2-benzisoselenazol-3(2H)-one is produced from 5.1 g. of o-chloroselenobenzoic acid chloride and 6.8 g. of 3-hydroxyaniline.

Yield: 2.5 g. (43% of the theoretical). F.p.: 195° to 197° C.

EXAMPLE 16
2-(2-Hydroxyphenyl)-1.2-benzisoselenazol-3(2H)-one

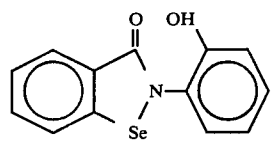

As described in Example 14, 2-(2-hydroxyphenyl)-1.2-benzisoselenazol-3(2H)-one is produced from 2 g. of o-chloroselenobenzoic acid chloride and 2.7 g. of 2-hydroaniline.

Yield: 0.91 g. (40% of the theoretical). F.p.: 194° to 196° C.

EXAMPLE 17

6-Fluoro-2-phenyl-1.2-benzisoselenazol-3(2H)-one

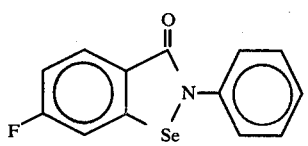

3.09 g. of 4-fluoro-2-methylselenobenzoic acid anilide are added dropwise with vivid stirring to a suspension of 4.16 g. of phosphorous pentachloride in 100 cc. of toluene. After termination of the addition, the resulting mixture is refluxed for two hours and thereafter is evaporated in a vacuum. The residue is triturated with anhydrous ethanol at 0° C. The resulting 3-chloro-6-fluoro-2-phenyl-1.2-benzisoselenazolium chloride is filtered off, suspended in a mixture of 20 cc. of water and 60 cc. of alcohol and heated to 70° C. until fully dissolved. The resulting solution is refluxed for one hour, thereafter evaporated and the resulting precipitate is filtered off and recrystallized from benzene/toluene.

Yield: 1.67 g. (57% of the theoretical). F.p.: 220° C.

As described in Example 17, the following compounds are prepared starting from the corresponding 2-methylselenobenzoic acid anilides:

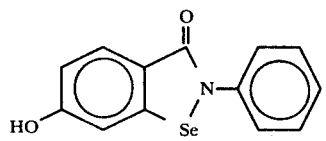

| Example No. | R | Emperical formula | Yield % of the theoretical | F.p.,°C. |
|---|---|---|---|---|
| 18 | 6-CH$_3$ | C$_{14}$H$_{11}$NOSe | 53 | 242 |
| 19 | 6-Cl | C$_{13}$H$_8$ClNOSe | 20 | 280 to 282 |
| 20 | 6-OCH$_3$ | C$_{14}$H$_{11}$NO$_2$Se | 40 | 189 |
| 21 | 5-NO$_2$ | C$_{13}$H$_8$ClNOSe | 42 | 273 |
| 22 | 5-Cl | C$_{13}$H$_8$ClNOSe | 10 | 247 |
| 23 | 7-OCH$_3$ | C$_{14}$H$_{11}$NO$_2$Se | 12 | 145 |
| 24 | -6.7-O—CH$_2$—O— | C$_{14}$H$_9$NO$_3$Se | 10 | 192 |

EXAMPLE 25

6-Hydroxy-2-phenyl-1.2-benzisoselenazol-3(2H)-one

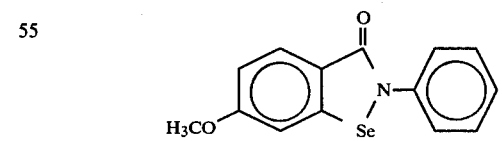

As described in Example 17, 6-benzyloxy-2-phenyl-1.2-benzisoselenazol-3(2H)-one is produced from 5.95 g. of 4-benzyloxy-2-methylselenobenzoic acid anilide and 6.2 g. phosphorus pentachloride.

Yield: 2.45 g. (43% of the theoretical). F.p.: 198° C.

As described in J. P. GREENSTEIN and M. WINITZ, Chemistry of the Amino Acids (1961), p. 2736, the benzyl group in this compound is split off with hydrogen in the presence of palladium and the resulting product is recrystallized from ethanol.

Yield: 16 g. (62% of the theoretical). F.p.: 235° C.

EXAMPLE 25a

5-Hydroxy-2-phenyl-1.2-benzisoselenazol-3(2H)-one

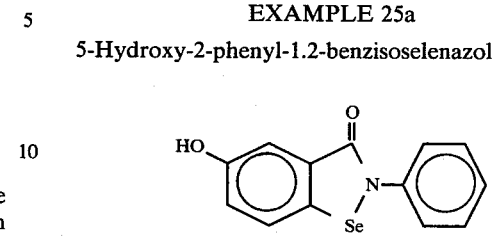

As described in Example 17, 5-benzyloxy-2-phenyl-1.2-benzisoselenazol-3(2H)-one is produced by reacting 4.1 g. of 5-benzyloxy-2-methylselenobenzoic acid anilide and 4.3 g. of phosphorous pentachloride.

Yield: 1.49 g. (38% of the theoretical). F.p.: 143° C.

As described in Example 25, the benzyl group is split off from this compound. The resulting product is recrystallized from ethanol.

Yield: 0.49 g. (43% of the theoretical). F.p.: 192° C.

EXAMPLE 26

2-(4-Trifluoromethylphenyl)-1.2-benzisoselenazol-3(2H)-one

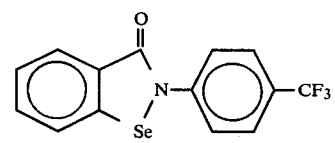

A solution of 0.44 g. of bromine in 10 cc. of dichloromethane are added dropwise at 0° C. under a nitrogen atmosphere to a solution of 1 g. of N-(4-trifluoromethylphenyl)-2-methylselenobenzoic acid amide in 40 cc. of dichloromethane. After termination of the addition, stirring is continued at room temperature for 30 minutes and the reaction mixture is evaporated under vacuum at 30° C. The resulting residue is mixed with 50 cc. of anhydrous acetic acid, the mixture refluxed for three hours and thereafter mixed with ice-water. The resulting precipitate is filtered off with suction and is recrystallized from ethanol/toluene.

Yield: 0.8 g. (84% of the theoretical). F.p.: 246° to 248° C.

EXAMPLE 27

6-Methoxy-2-phenyl-1.2-benzisoselenazol-3(2H)-one

A solution of 0.88 g. of bromine in 10 cc. of dichloromethane is added dropwise at 0° C. under a nitrogen atmosphere to a solution of 1.76 g. of N-phenyl-4-methoxy-2-methylselenobenzoic acid amide in 40 cc. of dichloromethane. After termination of the addition, the mixture is stirred for 30 minutes. The resulting precipitate is filtered off with suction and mixed with 20 cc. of pyridine. This mixture is refluxed for three hours and mixed with ice-water. The resulting crude material is recrystallized from ethanol/benzene.

Yield: 1.2 g. (72% of the theoretical). F.p.: 189° C.

EXAMPLE 28

2-(4-Phenylbutyl)-1.2-benzisoselenazol-3(2H)-one

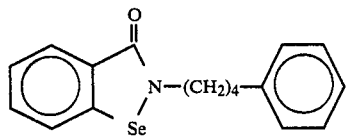

2-(4-Phenylbutyl)-1.2-benzisoselenazol-3(2H)-one is produced as described in Example 26 from 2 g. of N-(4-phenylbutyl)-2-methylselenobenzoic acid amide and 0.92 g. of bromine.

Yield: 1.26 g. (66% of the theoretical). F.p.: 97° to 99° C.

EXAMPLE 29

5-Nitro-2-phenyl-1.2-benzisoselenazol-3(2H)-one

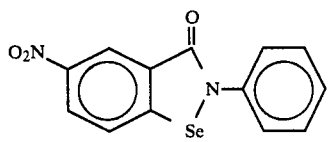

5-Nitro-2-phenyl-1.2-benzisoselenazol-3(2H)-one is produced as described in Example 27 from 1.2 g. of N-phenyl-5-nitro-2-methylselenobenzoic acid amide and 0.57 g. of bromine.

Yield: 0.81 g. (71% of the theoretical). F.p.: 273° C.

EXAMPLE 30

2-(3-Bromo-4-hydroxyphenyl)-benzisoselenazol-3(2H)-one

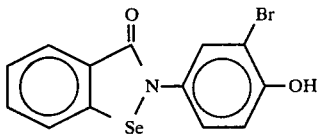

A solution of 0.53 g. of bromine in 500 cc. of acetic acid is added dropwise at room temperature under a nitrogen atmosphere to a solution of 1 g. of N-(4-hydroxyphenyl)-2-methylselenobenzoic acid amide in 40 cc. of acetic acid. After termination of the addition, stirring is continued at room temperature for one hour, the mixture is refluxed for two hours and thereafter is mixed with ice-water. The resulting precipitate is filtered off and is recrystallized from ethanol/benzene.

Yield: 0.58 g. (48% of the theoretical). F.p.: 232° to 234° C.

EXAMPLE 31

N-(4-Trifluoromethylphenyl)-2-methylselenobenzoic acid amide

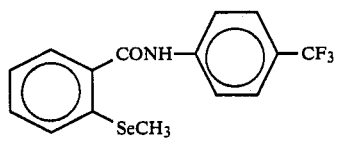

11.725 g. of 2-Methylselenobenzoic acid and 0.1 g. of anhydrous zinc-II-chloride are suspended in 50 cc of dichloromethane and 9.2 g. of α,α-dichloromethylether are added dropwise thereto. After one hour the resulting clear solution is evaporated in a vacuum, the oily residue is dissolved in carbontetrachloride, filtered with activated carbon and evaporated. The resulting 2-methylselenobenzoic acid chloride is dissolved in 50 cc. of tetrahydrofurane and added dropwise with ice-cooling to a solution of 8.86 g. of 4-trifluoromethylaniline in 70 cc. of tetrahydrofurane and 6 g. of triethylamine. The mixture is stored at room temperature for ten hours and thereafter is mixed with ice and dilute hydrochloric acid. The resulting precipitate is filtered off, dried and recrystallized from toluene/hexane.

Yield: 9.06 g. (82% of the theoretical). F.p.: 174° to 176° C.

As described in Example 31, the following methyl-selenobenzoic acid amides are produced from the corresponding aromatic acids and amines:

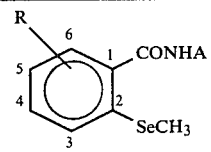

| Example No. | —R | —A | Emperical formula | F.p.,°C. |
|---|---|---|---|---|
| 32 | —H | —(CH₂)₄—⟨phenyl⟩ | C₁₈H₂₁NOSe | 61 to 62 |
| 33 | —H | —⟨phenyl⟩—OH | C₁₄H₁₃NO₂Se | 202 to 204 |
| 34 | —H | ⟨phenyl with HO⟩ | C₁₄H₁₃NO₂Se | 155 to 157 |

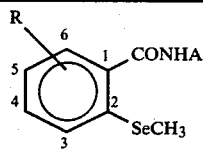

| Example No. | —R | —A | Emperical formula | F.p.,°C. |
|---|---|---|---|---|
| 35 | 5-Cl | —⟨phenyl⟩ | $C_{14}H_{12}ClNOSe$ | 167 to 170 |
| 36 | 4-Cl | —⟨phenyl⟩ | $C_{14}H_{12}ClNOSe$ | 175 |
| 37 | 4-F | —⟨phenyl⟩ | $C_{14}H_{12}FNOSe$ | 173 to 174 |
| 38 | 4-OCH$_3$ | —⟨phenyl⟩ | $C_{15}H_{15}NO_2Se$ | 154 to 155 |
| 39 | 4-CF$_3$ | —⟨phenyl⟩ | $C_{15}H_{12}F_3NOSe$ | 175 to 178 |
| 40 | 5-NO$_2$ | —⟨phenyl⟩ | $C_{14}H_{12}N_2O_3Se$ | 205 |
| 41 | 6-OCH$_3$ | —⟨phenyl⟩ | $C_{15}H_{15}NO_2Se$ | 138 to 140 |
| 42 | 4-CH$_3$ | —⟨phenyl⟩ | $C_{15}H_{15}NOSe$ | 175 |
| 43 | 3-OCH$_3$ | —⟨phenyl⟩ | $C_{15}H_{15}NO_2Se$ | 129 |
| 44 | 3.4-O—CH$_2$—O— | —⟨phenyl⟩ | $C_{15}H_{13}NO_3Se$ | 150 to 153 |

EXAMPLE 45

Tablets

| | |
|---|---|
| 2-(4-chlorophenyl)-1.2-benzisoselenazol-3(2H)-one | 30 mg. |
| lactose | 150 mg. |
| cristalline cellulose | 50 mg. |
| calciumcarboxymethyl cellulose | 7 mg. |
| magnesium stearate | 3 mg. |

The above ingredients are mixed and pressed to tablets in usual manner using usual equipment. If desired, the resulting tablets may be coated with a usual coating.

EXAMPLE 46

Tablets

| | |
|---|---|
| 2-(4-fluorophenyl)-1.2-benzisoselenazol-3(2H)-one | 30 mg. |
| lactose | 150 mg. |
| cristalline cellulose | 50 mg. |
| calciumcarboxymethyl cellulose | 7 mg. |
| magnesium stearate | 3 mg. |

The resulting ingredients are mixed and pressed in usual manners using usual equipment. If desired, the resulting tablets may be coated with a usual coating.

EXAMPLE 47

Tablets

| | |
|---|---|
| 2-(4-hydroxyphenyl)-1.2-benzisoselenazol-3(2H)-one | 30 mg. |
| lactose | 150 mg. |
| cristalline cellulose | 50 mg. |
| calciumcarboxymethyl cellulose | 7 mg. |
| magnesium stearate | 3 mg. |

The resulting ingredients are mixed and pressed in usual manners usinf usual equipment. If desired, the resulting tablets may be coated with a usual coating.

EXAMPLE 48

Tablets

| | |
|---|---|
| 2-(4-trifluorophenyl)-1.2-benzisoselenazol-3(2H)-one | 50 mg. |
| microcristalline cellulose | 150 mg. |
| Cutina HR | 15 mg. |

-continued

| | |
|---|---|
| hydroxypropylmethyl cellulose phthalate | 20 mg. |

EXAMPLE 49

Tablets

| | |
|---|---|
| 2-(4-cyanophenyl)-1.2-benzisoselenazol-3(2H)-one | 50 mg. |
| microcristalline cellulose | 150 mg. |
| Cutina HR | 15 mg. |
| hydroxypropylmethyl cellulose phthalate | 20 mg. |

EXAMPLE 50

Capsules

| | |
|---|---|
| 2-(4-phenylbutyl)-1.2-benzisoselenazol-3(2H)-one | 30 mg. |
| lactose | 102 mg. |
| cristalline cellulose | 56 mg. |
| colloidal silicic dioxide | 2 mg. |

The above ingredients are mixed, granulated, and filled into hard gelatine capsules in usual manners using usual equipment.

EXAMPLE 51

Capsules

| | |
|---|---|
| 5-fluor-2-phenyl-1.2-benzisoselenazol-3(2H)-one | 30 mg. |
| lactose | 102 mg. |
| cristalline cellulose | 56 mg. |
| colloidal silicic dioxide | 2 mg. |

The above ingredients are mixed, granulated and filled into hard gelatine capsules in usual manners using usual equipment.

EXAMPLE 52

Capsules

| | |
|---|---|
| 5-chloro-2-phenyl-1.2-benzisoselenazol-3(2H)-one | 50 mg. |
| talcum | 5 mg. |
| aerosil | 10 mg. |

The above ingredients are mixed, granulated and filled into hard gelatine capsules in usual manners using usual equipment.

What we claim is:

1. A benzisoselenazolone having the general formula I

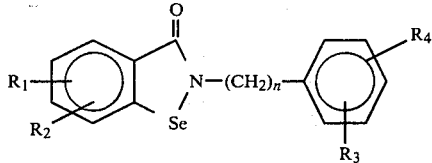

wherein $R_1$ and $R_2$ which may be the same or different from each other, represent hydrogen, fluorine, chlorine, bromine, $C_1$ to 4-alkyl, $C_1$ to 4-alkoxy, hydroxy, trifluoromethyl, nitro, or $R_1$ and $R_2$ together represent the methylenedioxy group —O—$CH_2$—O—, $R_3$ and $R_4$ which may be the same or different from each other, represent hydrogen, fluorine, chlorine, bromine, $C_1$ to 4-alkyl, $C_1$ to 4-alkoxy, hydroxy, trifluoromethyl, nitro, di-($C_1$ to 4-alkyl)-amino or, $R_3$ and $R_4$ together, represent the methylenedioxy group —O—$CH_2$—O— or $R_3$ represents hydrogen with $R_4$ being —CN, —$COOR_5$ or

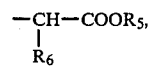

wherein $R_5$ is hydrogen, an alkali metal ion or $C_1$ to 4-alkyl and $R_6$ being hydrogen, methyl or ethyl, and n is 0 or an integer from 1 to 4, with the exclusion of the compounds of formula I, wherein n is 0, $R_1$, $R_2$ and $R_3$ are hydrogen and $R_4$ is hydrogen or o-methyl or n is 1 and $R_1$, $R_2$, $R_3$ and $R_4$ are hydrogen.

2. A benzisoselenazolone as claimed in claim 1 wherein in formula I n is 0 and either $R_1$ and $R_2$ or $R_1$ and $R_3$ represent hydrogen with the other substituents being fluorine, chlorine, bromine, hydroxy, methoxy, methyl, trifluoromethyl and/or nitro.

3. A benzisoselenazolone as claimed in claim 1 wherein in formula I n is 0 or an integer from 1 to 4, $R_1$, $R_2$ and $R_3$ represent hydrogen and $R_4$ is —CN, —$COOR_5$ or

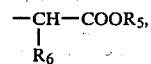

$R_5$ being H, $Na^{\oplus}$, —$CH_3$ or —$C_2H_5$ and $R_6$ being H, —$CH_3$ or —$C_2H_5$.

4. Process for the treatment of inflammation symptoms of rheumatic and arthritic diseases comprising administering to the being suffering from such disease a compound according to claim 1, 2 or 3 in an amount corresponding to 10 to 1000 mg. per day until the desired degree of alleviation of the symptoms of such disease is achieved.

* * * * *